United States Patent
He et al.

(10) Patent No.: US 10,245,353 B2
(45) Date of Patent: Apr. 2, 2019

(54) HYDROPHILIC ELECTROSPINNING BIOLOGICAL COMPOSITE STENT MATERIAL USED FOR TISSUE REGENERATION AND PREPARATION METHOD AND APPLICATION THEREOF

(71) Applicant: Shanghai P & P Biotech Co., Ltd, Minhang District, Shanghai (CN)

(72) Inventors: Hongbing He, Shanghai (CN); Ling Su, Shanghai (CN); Zhang Liu, Shanghai (CN); Li Yang, Shanghai (CN)

(73) Assignee: Shanghai P & P Biotech Co., Ltd, Shanghai (CN)

( * ) Notice: Subject to any disclaimer, the term of this patent is extended or adjusted under 35 U.S.C. 154(b) by 88 days.

(21) Appl. No.: 15/037,507

(22) PCT Filed: Nov. 19, 2013

(86) PCT No.: PCT/CN2013/087396
§ 371 (c)(1),
(2) Date: May 18, 2016

(87) PCT Pub. No.: WO2015/074176
PCT Pub. Date: May 28, 2015

(65) Prior Publication Data
US 2016/0279301 A1    Sep. 29, 2016

(51) Int. Cl.
*D01D 5/00* (2006.01)
*D01F 1/10* (2006.01)
(Continued)

(52) U.S. Cl.
CPC ........... *A61L 31/046* (2013.01); *A61L 31/041* (2013.01); *A61L 31/16* (2013.01); *D01D 5/0007* (2013.01);
(Continued)

(58) Field of Classification Search
None
See application file for complete search history.

(56) References Cited

U.S. PATENT DOCUMENTS

| 1,975,504 A | 10/1934 | Formhals |
| 5,861,168 A * | 1/1999 | Cooke ............... A61K 31/00 424/424 |

(Continued)

FOREIGN PATENT DOCUMENTS

| CN | 101502671 A | 8/2009 |
| CN | 101574543 A | 11/2009 |

(Continued)

OTHER PUBLICATIONS

Bertolini et al. "Production of Plasma Proteins for Therapeutic Use", John Wiley & Sons, Dec. 2012, pp. 124 and 125.*

(Continued)

*Primary Examiner* — Carlos A Azpuru
*Assistant Examiner* — Casey S Hagopian
(74) *Attorney, Agent, or Firm* — Panitch Schwarze Belisario & Nadel LLP

(57) ABSTRACT

A hydrophilic electrospinning biological composite scaffold material used for tissue regeneration and a preparation method and an application thereof are provided. Fibrinogen, L-arginine or an aqueous solution of hydrochloride thereof and a P(LLA-CL) solution are blended and an electrospinning technology is used to prepare the biological composite scaffold material. The biological composite scaffold material has an equilibrium contact angle that is less than 55°, is hydrophilic and has a good application prospect in repairing body tissue defects.

25 Claims, 3 Drawing Sheets

(51) Int. Cl.
| | |
|---|---|
| D01F 6/62 | (2006.01) |
| D01F 6/84 | (2006.01) |
| A61L 31/04 | (2006.01) |
| A61L 31/16 | (2006.01) |
| C08L 67/04 | (2006.01) |
| C08L 89/00 | (2006.01) |

(52) U.S. Cl.
CPC ............... *D01F 1/10* (2013.01); *D01F 6/625* (2013.01); *D01F 6/84* (2013.01); *A61L 2300/404* (2013.01); *A61L 2430/06* (2013.01); *A61L 2430/10* (2013.01); *A61L 2430/22* (2013.01); *D10B 2401/022* (2013.01); *D10B 2509/06* (2013.01)

(56) References Cited

U.S. PATENT DOCUMENTS

| | | | |
|---|---|---|---|
| 8,236,538 B2 * | 8/2012 | Harmon | A61L 2/0011 422/22 |
| 8,481,074 B2 | 7/2013 | Shalaby et al. | |
| 2003/0208258 A1 * | 11/2003 | Reilly | A61F 2/06 623/1.13 |

FOREIGN PATENT DOCUMENTS

| | | | |
|---|---|---|---|
| CN | 101780292 A | * | 7/2010 |
| CN | 101780292 A | | 7/2010 |

OTHER PUBLICATIONS

Li et al. "One-Dimensional Nanostructures, Electrospinning Technique and Unique Nanofibers", Springer, 2013, pp. 15-28.*
Dong et al., Machine translation of CN 10178292 A (Jul. 2010).*
Bertolini et al. "Production of Plasma Proteins for Therapeutic Use", John Wiley & Sons, Dec. 2012, pp. 124 and 125. (Year: 2012).*
Li et al. "One-Dimensional Nanostructures, Electrospinning Technique and Unique Nanofibers", Springer, 2013, pp. 15-28. (Year: 2013).*
Dong et al., Machine translation of CN 10178292 A (Jul. 2010). (Year: 2010).*
"Amino Acid Properties", International Agency for Research on Cancer, World Health Organization, accessed online on Sep. 4, 2018 at http://p53.iarc.fr/AAProperties.aspx. (Year: 2018).*
Int'l Search Report dated Aug. 22, 2014 issued in Int'l Application No. PCT/CN2013/087396.
He et al., "Fabrication of Fibrinogen/P(LLA-CL) Hybrid Nanofibrous Scaffold for Potential Soft Tissue Engineering Applications", Journal of BioMedical, vol. 97a, No. 3, pp. 339-347 (Jun. 1, 2011).

* cited by examiner

HYDROPHILIC ELECTROSPINNING BIOLOGICAL COMPOSITE STENT MATERIAL USED FOR TISSUE REGENERATION AND PREPARATION METHOD AND APPLICATION THEREOF

CROSS-REFERENCE TO RELATED APPLICATION

This application is a Section 371 of International Application No. PCT/CN2013/087396, filed Nov. 19, 2013, which was published in the Chinese language on May 28, 2015, under International Publication No. WO 2015/074176 A1 the disclosure of which is incorporated herein by reference.

TECHNICAL FIELD

The present invention relates to a hydrophilic electrospinning biological composite scaffold scaffold material used for tissue regeneration and preparation method and application thereof, and specifically relates to a hydrophilic biological composite scaffold material prepared from fibrinogen, L-arginine (hydrochloride) and polylactic acid-polycaprolactone (P (LLA-CL)) as raw materials by using an electrospinning technique, and preparation method and application thereof in repairing body tissue defects. The present invention belongs to a field of medical health.

BACKGROUND

Tissue engineering is an emerging interdisciplinary which studies the tissues and organs of a biological organism or functional substitutes thereof using the principles and approaches of engineering science and bioscience. The basic principles and approaches of tissue engineering are that cells are absorbed in vivo or in vitro on a scaffold with good biocompatibility, which is prepared from synthetic polymers and/or natural polymers (e.g. extracellular matrix) and can be adhered by an organism gradually, to form a cell-biological materials complex. After the scaffold is degraded and absorbed, the complex performs corresponding functions at a specific anatomical position in the body, meanwhile, the host cells proliferate, secrete new extracellular matrix, and finally a new tissue or organ having a function and shape corresponding to those of the original anatomical position is formed, thereby achieving the purpose of repairing tissue shapes and rebuilding functions. Tissue engineering comprises three elements, viz., specific tissue cells, a scaffold and extracellular matrix. The scaffold not only plays a central role since it not only can provide a structural support for the specific cells, but also can function as a template to guide tissue regeneration and control tissue structure.

The extracellular matrix of tissues of animals including humans is a complex of nano-sized fibrous proteins, polysaccharides and proteoglycans, and may be imitated using nanofiber structures. With the advent of nano-era, reports on nanofiber increase rapidly. The preparation methods of nanofiber can be classified into chemical methods, physical methods and electrical methods. The chemical methods are based on the principle of molecular self-assembly by which small molecules with specific structures may be assembled into fibrous macromolecules. The physical methods are that the nanofiber can be obtained by performing lyophilization of L-polyactic acid solution to remove solvent utilizing special sol-gel property of L-polyactic acid when it reaches the liquid-liquid phase equilibrium through. It is difficult to obtain large quantities of products through the chemical method, and the physical methods are only limited to the preparation of L-polyactic acid nanofibers. The electrical methods, which utilize the electrospinning technique, are that a macromolecular solution is charged under a high-voltage electrostatic field and made into filaments during ejection toward a low-voltage electrical field. In theory, if there is a suitable solution system for polymers, they all can be made into nanofibers by using the electrospinning technique, and batch production can be preformed.

In 1934, Formhals (U.S. Pat. No. 1,975,504) firstly reported a patent for the electrospinning technique. However, only in the last decade, the application of electrospinning filaments in tissue repair has been studied. Therefore, the understanding of design and preparation of the electrospinning filaments and their in vivo or in vitro interaction with cells at molecular and cellular level is rather superficial. The successful application of the electrospinning filament in clinical practice has barely been reported.

Synthetic polymers used in the preparation of electrospinning filaments may be degradable aliphatic polyesters such as polylactic acid (PLA), poly(lactic-co-glycolic acid) (PLGA), polycaprolactone (PCL), and copolymers or mixture thereof. Under electrospinning conditions, these traditional materials can be conveniently made into polymer microfibers having a diameter from tens of nanometers to hundreds of nanometers, which are very similar to the major component of natural extracellular matrix, i.e. collagen, and have the following advantages: (1) imitating the structure of ECM in the body to the greatest extent; (2) having a higher porosity and extremely large volume-surface ratio, which facilitate the adhesion, differentiation, proliferation of cells, the secretion of ECM and the like; (3) perfectly controlling the thickness, three-dimensional structure and mechanical properties of electrospinning filaments by adjusting the concentration of solutions, electrospinning parameters and the like, and thereby facilitating cell growth, nutrient absorption and the excretion of metabolites; and (4) conveniently preparing electrospinning filaments from one or more the above-mentioned polymers.

Related studies have found that electrospinning of pure synthetic polymer has the following defects: (1) the filaments, compared with those prepared from natural polymers, lack cell recognition sites, and thus it is difficult for cells to adhere thereto; (2) the filaments inherently possess hydrophobicity and thus have poor hydrophilicity (for example, polycaprolactone (PCL) and polylactic acid-polycaprolactone (PLLA-CL) have a water contact angle of 109-120° and 109-133°, respectively), which seriously affects the adhesion of cells and subsequent cell activities; and (3) the degradation products of PLA and PGA are relatively strong acids (lactic acid or glycolic acid), and once these degradation products accumulates around a implant, delayed inflammatory reaction will appear in a few months or years. Thus, although electrospinning of synthetic polymer has a porosity which is 1-2 orders of magnitudes higher than conventional methods (such as air bubbling method and freeze drying method) and have a very high volume-surface ratio, the low hydrophilicity renders most pores empty, and thereby the three dimensional structure cannot be utilized efficiently.

To solve the above-mentioned problems, there is an urgent need to develop new electrospinning filaments having biological activities and functions. The biological activities refer to a material formed by the physical (such as mixing) or chemical (such as covalent immobilization) combination of biologically active substances and the structure or function of this material may, in vivo and/or in vitro, have positive effects on living cells, and facilitate the interaction between cells and the scaffold, such as proliferation, migration and maintenance of the shape and function of normal cells, which relates to the inherent biochemical properties of the used materials. Natural polymers such as proteins (collagen, silk fibroin, gelatin, elastin) and polysaccharides (chitosan, hyaluronic acid) are most ideal. In recent years, blood-derived fibrinogen (Fg) has drawn increasing attention. However, the major problems of natural polymers after electrospinning treatment lies in that: 1) they have low mechanical strength and are degraded with a too fast speed after implantation, and thus post-processing is often required, such as cross linking by glutaraldehyde vapor or UV irradiation, which finally renders the products swollen in water or inside the body without degradation; formaldehyde treatment, which drives a transition of fibres from random coil to beta sheet, improves the degree of crystallinity and decreases porosity, making them have a more compact structure; or alkali treatment on natural polysaccharide biopolymers (such as chitin and cellulose), which improves mechanical strength and prolongs degradation time; (2) after the above-mentioned post-processing, the mechanical strength of the natural polymers is improved significantly, but the largest problem brought about by such post-processing is that the degradation speed is reduced and the natural polymers even cannot be degraded. As a scaffold material, its major function is assisting in wound healing-related protein adsorption and cell adhesion thereto as a temporary transitional substance, and thereby the purpose of tissues remodeling may be achieved by cell ingrowth and the secretion of its own extracellular matrix. Thus, the reduction or loss of degradation speed will seriously affect subsequent tissue regeneration process.

The generation of composite electrospinning filaments brings a new idea for overcoming the defects of electrospinning of pure synthetic polymers and natural polymers and retaining their respective advantages. Composite electrospinning filaments may change the surface properties of scaffold materials easily and economically. In theory, they have the following advantages: in terms of physical aspect, they improve the hydrophility and mechanical strength of new composite scaffold materials; and in terms of a biological aspect, after biological molecules binding to the synthetic polymers, they may facilitate recognition of surfaces of the material by cells and facilitate or control many physiological activities of cells, such as adhesion, expansion, activation, migration, proliferation and differentiation.

Research results indicate that, although electrospinning filaments prepared from synthetic-natural polymers, compared with those prepared from pure natural polymers or natural polymers, have been improved in their physical or biological properties, they are still far away from clinical requirements. One of the reasons for this is that the contact of the electrospinning filaments prepared from synthetic polymers (such as polylactic acid-polycaprolactone (P(LLA-CL)), PLC or PCL) and natural biopolymers (such as collagen, elastin and chitosan), with an aqueous solution, often gives rise to shrinkage of composite scaffold materials with a shrinkage ratio of up to 20-50%. The change of this characteristic directly affects the porosity, degradation speed, wettability and the like of the electrospinning filaments. So far, there have been no reports on the successful clinical application of such biological composite scaffold materials.

CN101780292A discloses a Fg-based three-dimensional porous nano-scaffold and a method for preparing the same. The three-dimensional porous nano-scaffold is prepared from Fg and polylactic acid/polycaprolactone with a mass ratio (Fg:polylactic acid/polycaprolactone) of 1:5-12:5.

Fg, a biomacromolecule with a relative molecular weight of 340,000, is composed of three pairs of peptide chains (α-chain, β-chain, and γ-chain), and its subunits are linked together as a whole via three disulfide bonds. Since Fg is extracted from plasma, it has good histocompatibility. Meanwhile, Fg is degraded by fibrinolysin in a body, and degradation products are no longer involved in blood coagulation, and finally are eliminated by body tissues. The biological functions of Fg lie in that: (1) it has hemostatic effect, i.e. under physical conditions, Fg is converted to fibrin to form a blood clot, thereby achieving hemostatic effect; (2) it functions as a scaffold carrier of cells, i.e. a fibrin-based scaffold material may deliver cells to different defect or coloboma sites, for example, human smooth muscle cells may proliferate well inside or on the surface of a blood clot, and likewise, fibrin glue may make normal human-derived keratinocytes and fibroblasts have good proliferation results; (3) fibrin acts as a carrier for the delivery of cytokines and peptides in an active way: some growth factors, such as basic fibroblast growth factor (bFGF) and vascular endothelial growth factor, may bind to fibrin with strong binding and meanwhile may slowly diffuse from a blood clot; and insulin-like growth factor 1 and transforming growth factor β may be directly embedded in fibrin scaffolds during polymerization, protecting those these growth factors from denaturation and degradation by proteasomes in vivo and in vitro. Fibrin, comprises RGDS and RGDF bioactive peptides at Aα572-575 and 95-98, respectively, with which cells interact via the mediation of integrin and induce cellular signal transduction; and in addition, fibrin may be linked with antibiotics, painkillers and the like, and when fibrinogen is used to stop bleeding and to seal tissues, local affection and pain may be controlled in 1-2 weeks, which happens to be the degradation period of fibrin clots and during which fibrin may retain many bioactive substances in an active and effective way and position them locally to facilitate tissue repairing.

Further studies indicate that electrospinning filaments prepared from P(LLA-CL) and Fg with the ratio of 10:0, 8:2 and 0:10 (P(LLA-CL): Fg) have the water contact angles of 110°, 95° and 65°, respectively (see, Chuanglong He, The potential applications of the preparation of Fg/polylactic acid-polycaprolactone hybrid nanofiber scaffolds in soft tissue engineering). Similar research results may also be found in Fabrication of fibrinogen/P(LLA-CL)hybrid nanofibrous scaffold for potential soft tissue engineering applications, *Journal of Biomedical Materials Research A*, 97A (3):339-347(2011). In modern material science, it is recognized that when a material has a water contact angle of more than 65°, the surface wettability of the material is hydrophobicity.

A lot of studies prove that, for both the degradation of a scaffold material and the regeneration of host tissues, the surface wettability of a solid material is an important factor for regulating the balance of the two processes. In the surface chemistry of a material, it is a common phenomenon that water can wet some surfaces, on the contrary, it cannot wet some other surfaces, but forms liquid drops thereon with a limited "contact angle". Such solid surface wetting phenomenon has driven material scientists to conduct researches for almost three centuries. Generally, the surface wettability of a solid material is measured as water contact angles. The contact time between liquid drops and polymers greatly affects the measured value of a contact angle. The contact angle formed when the liquid drops contact the polymer surface for the very first time, is referred to as initial contact angle, which rapidly decreases within 10-20 minutes, and when the contact angle no longer changes over time and reaches a constant value, it is referred to as equilibrium contact angle. When the equilibrium contact angle between a solid surface and water is more than 65°, the solid surface is referred to as hydrophobic surface, and when the equilibrium contact angle is more than 150°, the solid surface is referred to as super-hydrophobic surface; and when the equilibrium contact angle is less than 55°, the solid surface is referred to as hydrophilic surface, and when the equilibrium contact angle is less than 5°, the solid surface is referred to as super-hydrophilic surface. It is believed that, after P(LLA-CL) and Fg are blended with a certain ratio, the cell recognition sites on the surface of the prepared electrospinning filaments are improved substantially, but the water contact angle decreases from 110° of pure P(LLA-CL) to 65°, and thus the obtained material still belongs to hydrophobic materials. Just as described above, the hydrophobicity of a material will hinder the degradation in vivo and vitro, protein absorption and cell adhesion, affect the ingrowth of cells, especially blood capillaries, and have the following impacts: oxygen, nutrients, antibodies, immune cells and related antibacterial substances cannot be supplemented effectively; acidic metabolites cannot be successfully eliminated timely; and microorganisms (such as skin or blood-derived bacteria) aggregate locally and cannot be inhibited and eliminated effectively, the occurrence rate of infection may thus be up to 20-30%. The decrease or loss of tissue regeneration speed and the occurrence of local infection are main reasons for the recurrence of tissue defect diseases after repairing (such as recurrence after a hernia repair and recurrence after a pelvic organ prolapse repair). Therefore, how to effectively improve the hydrophility of electrospinning filaments is a key problem to be solved.

In conclusion, although a patent has been disclosed for the principle of the electrospinning technique in 1934, the electrospinning biological composite scaffold material has drawn more and more attention since tissue engineering has been booming in the last decade. Theoretically, the material has a network structure similar to that of connective tissue of a body and thus should have a promising application prospect. However, so far, the successful application of electrospinning biological composite scaffold material in clinical practice has not been reported, the reasons for which is greatly related to the superficial understanding of structure materials of this kind. The problems to be solved mainly include (1) how to improve the protein and cell recognition site of synthetic polymers; (2) how to improve the surface property of a material, especially wettability; (3) how to effectively reduce the common shrinkage phenomenon of the electrospinning biological composite scaffold material after contacting with an aqueous solution; and (4) how to effectively prevent bacterial infections with a occurrence rate up to 20-30%, and a high recurrence rate.

DISCLOSURE OF THE INVENTION

One object of the present invention is to provide an electrospinning composite scaffold material which may effectively facilitate wound healing-related protein absorption thereto and regeneration and repair-related cell adhesion thereto in vitro and in vivo. Such material may effectively prevent the formation of bacterial biofilm to ensure that it exerts corresponding functions at a specific anatomical position in vivo; Such material have suitable degradation speed and regeneration ability. When the biological scaffold is degraded and absorbed, the host cells proliferate, secrete new extracellular matrix, and finally form a new tissue and organ having functions and shapes corresponding to those of the original anatomical position, thereby achieving the purpose of repairing tissue shapes and rebuilding functions.

Another object of the present invention is to provide a method of preparing the electrospinning composite scaffold material.

Still another object of the present invention is to provide applications of the electrospinning composite scaffold material, especially applications of the electrospinning composite scaffold material for use as a material for repairing body tissue defects or for use in the preparation of a material for repairing body tissue defects.

In order to ensure the achievement of the above-mentioned objects, the provided scaffold material must have good hydrophility. Therefore, the water contact angle of the surface of the material should be less than 55°, preferably less than 5°. Moreover, the scaffold material must have enough mechanical strength during degradation so as to prevent corresponding tissues and organs at tissue defect sites from prolapse, expansion and rupture. In addition, after contacting with an aqueous solution or tissue fluid, the scaffold material would not shrink with the shrinkage ratio not being more than 20%.

In one aspect, the present invention provides a hydrophilic electrospinning biological composite scaffold material prepared by blending an aqueous solution of fibrinogen (Fg) and L-arginine or hydrochloride thereof with a P(LLA-CL) solution using an electrospinning technique.

The inventors have surprisingly found that the electrospinning filaments prepared after blending according to different mass ratios of P(LLA-CL): the aqueous solution of fibrinogen (Fg) and L-arginine or hydrochloride thereof, have an equilibrium contact angle decreasing from 110° of pure P(LLA-CL) and more than 65° of P(LLA-CL)/Fg to below 55° with significant hydrophility; and further decreasing to below 5° with super-hydrophility.

The hydrophilic electrospinning biological composite scaffold material prepared by blending an aqueous solution of fibrinogen (Fg) and L-arginine and a P(LLA-CL) solution together using an electrospinning technique, provided in the present invention, has an shrinkage ratio of not more than 20% and an porosity of not less than 30% after contacting with an aqueous solution.

According to specific embodiments of the present invention, in the hydrophilic electrospinning biological composite scaffold material according to the present invention, the Fg is derived from Fg of mammals. The mammals include, but not limited to, human, pigs, cattle, sheep or horses and the like.

According to a specific embodiment of the present invention, in the hydrophilic electrospinning biological composite scaffold material according to the present invention, the mass ratio of Fg to L-arginine or hydrochloride thereof in the aqueous solution of Fg and L-arginine or hydrochloride thereof is 1.2:1-12.5:1.

According to specific embodiments of the present invention, in the hydrophilic electrospinning biological composite scaffold material according to the present invention, the mass ratio of polylactic acid to polycaprolactone in the P(LLA-CL) is 20:80-95:5. In the present invention, there is no other specific requirements for other properties of the P(LLA-CL) as long as the P(LLA-CL) meets corresponding industry standards.

According to specific embodiments of the present invention, in the hydrophilic electrospinning biological composite scaffold material according to the present invention, the solvents of the aqueous solution of Fg and L-arginine or hydrochloride thereof may be one or more solvents selected from pure water, water for injection, various salt solutions (including but not limited to sodium chloride solution, potassium chloride solution and the like), various buffers (including but not limited to phosphate buffer, Tris-HCl buffer, glycine buffer, D-Hank's solution and the like) and various cell culture media (including but not limited to DMEM medium, 1640 medium, MEM medium and the like). That is to say, the aqueous solution of Fg and L-arginine or hydrochloride thereof according to the present invention may be aqueous solutions obtained by dissolving Fg and L-arginine or hydrochloride thereof in pure water, water for injection, various salt solutions, various buffers, various cell culture media and the like.

According to specific embodiments of the present invention, in the hydrophilic electrospinning biological composite scaffold material according to the present invention, the solvents of the P (LLA-CL) solution may be various organic solvents, for example, may be one or more solvents selected from hexafluoroisopropanol, trichloromethane, dimethylformamide, tetrahydrofuran, chloroform or acetone and the like.

According to specific embodiments of the present invention, in the hydrophilic electrospinning biological composite scaffold material according to the present invention, after the aqueous solution of Fg and L-arginine or hydrochloride thereof is blended with the P(LLA-CL) solution, the mass ratio of Fg:P(LLA-CL) is 0.2:1-2.1:1.

According to specific embodiments of the present invention, in the hydrophilic electrospinning biological composite scaffold material according to the present invention, the aqueous solution of Fg and L-arginine or hydrochloride thereof may further be loaded with various antibacterial substances, including but not limited to one or more selected from penicillins (penicillin, ampicillin, carbenicillin and the like), cephalosporins (cephalexin, cefuroxime sodium, ceftriaxone, cefpirome and the like), carbapenms (such as thiomycin), aminoglycosides (gentamicin, streptomycin, kanamycin and the like), tetracyclines (such as tetracycline, chlortetracycline and the like), macrolides (such as erythromycin, azithromycin and the like), glycosides (such as vancomycin), sulfonamides (such as sulfadiazine and trimethoprim), quinolones (such as pipemidic acid and ciprofloxacin), nitroimidazoles (such as metronidazole and tinidazole), lincosamides (such as lincomycin and clindamycin), phosphonomycin, chloromycetin, polymyxin B and bacitracin. More specifically, the antibacterial substances is added in an amount such that the release amount thereof is preferably not less than 30% of the total load amount within 15 minutes after the implantation of the scaffold material.

According to specific embodiments of the present invention, the shape of the hydrophilic electrospinning biological composite scaffold material according to the present invention may be selected as needed. For example, the shape of the material may be membranous and preferably the thickness thereof is 10-1500 μm, more preferably 50-500 μm. The shape of the material may be tubular, and preferably the tube wall thickness thereof is 1-1500 μm, more preferably 50-500 μm, and the internal diameter thereof is 2-200 mm. The shape of the material is columnar, and the diameter thereof is preferably 2-20 mm.

In another aspect, the present invention further provides the method of preparing the hydrophilic electrospinning biological composite scaffold material, comprising: blending an aqueous solution of Fg and L-arginine or hydrochloride with a P(LLA-CL) solution and subjecting the obtained solution to electrospinning by using an electrospinning technique, to prepare the biological composite scaffold material.

According to specific embodiments of the present invention, the electrospinning technique in the preparation method according to the present invention may be carried out by making reference to the prior art of the field to which the present invention pertains. The parameters for an electrospinning machine in the present invention are preferably set as follows: electrospinning distance of 10-30 cm; electrospinning voltage of 15-70 kV; and solution flow rate of 2-400 ml/h.

According to specific embodiments of the present invention, the preparation method according to the present invention may further comprise performing the sterilization of the prepared biological composite scaffold material by using 15-35 KGy ionizing radiation.

When specific operations are performed, the blend solution of the aqueous solution of Fg and L-arginine or hydrochloride thereof with P(LLA-CL) solution may be loaded into the electrospinning machine, and rod-shaped materials with a diameter of 1-20 mm (used to prepare tubular materials) or removable surfaces (used to prepare membranous materials) are used as collection devices. The parameters for the electrospinning machine are set as follows: electrospinning distance of 10-30 cm; electrospinning voltage of 15-70 kV; and solution flow rate of 2-400 ml/h. After electrospinning, the electrospinning composite material is intactly taken from the collection device, subjected to post-processes such as cutting, setting, packaging and sterilization (degerming), and then stored at 2-8° C.

In another aspect, the present invention further provides applications of the hydrophilic electrospinning biological composite scaffold material, especially applications of the hydrophilic electrospinning biological composite scaffold material for use as a material for repairing body tissue defects, or for use in the preparation of a material for repairing body tissue defects.

The biological composite scaffold material according to the present invention has hydrophility or super-hydrophility, and such hydrophilic electrospinning filaments, after implantation, have the following advantages:

(1) the surface wettability of the biological composite scaffold material is greatly improved with a change from hydrophobicity to (super-) hydrophility; and the common shrinkage phenomenon of the biological composite scaffold material after contacting with a water solution is effectively overcome, which phenomenon will greatly affect the porosity, hydrophility and degradation and regeneration speed of the biological composite scaffold material;

(2) one of the important reasons why traditional pure natural polymers fails to be used as regeneration material in clinic is that an occurrence rate of bacterial infection up to 20-30% leads to serious inflammatory response at an implantation site, slow ingrowth of wound repair cells, insufficient local supply of oxygen and nutrients, disorder of metabolite excretion and extremely great influence on tissue remodeling process, and thereby resulting in the recurrence caused by poor repair of local defect tissue. When the electrospinning biological composite scaffold material prepared according to the present invention is used, the occurrence rate of bacterial infection is less than 1% and the main reasons are as follows: ① bacteria generally have hydrophobic surfaces and thus have difficulty in adhering to hydrophilic material surfaces; ②further, due to the (super-) hydrophility of the composite scaffold material according to the present invention, more than 30% of the loaded antibacterial substances may be released within 15 minutes, and an antibacterial barrier at a high concentration is formed locally at the implantation site; and ③with suitable degradation and regeneration speed, they facilitate the ingrowth of blood capillaries, the local aggregation of immune cells and antibodies and the timely elimination of metabolites, and facilitate the effective local elimination of pathogenic microorganisms to reduce the occurrence rate of infection;

(3) as Fg is used as one raw material of electrospinning, the network structure overcomes the defect of pure synthetic polymers, viz. lacking cell recognition sites; Fg, a trauma-initiating protein, may attract and bind to wound healing-factors (such as platelet-derived growth factor PDGF, vascular endothelial growth factor VEGF and fibroblast growth factor FGF), recruit wound healing-cells (such as fibroblasts and endothelial cells), and play positive roles in the degradation of synthetic polymers, the ingrowth of blood capillaries and the remodeling of local tissues.

According to specific embodiments of the present invention, the biological composite scaffold material of the present invention may have different shapes and sizes depending on the specific application. For example, when the biological composite scaffold material is membranous, it usually may be used in the preparation of repair materials for the treatment of meninges defects, abdominal defects (such as inguinal hernia, umbilical hernia and incisional hernia), pelvic organ prolapse, atrium defects, ventricular septum defects, pericardium defects, tendon rupture or ligament rupture and the like, or ruptures of parenchymatous organs (such as liver, spleen, kidney and pancreas). When the biological composite scaffold material is tubular, it generally may be used to prepare materials for repairing tubular organs including one or more selected from nerve conduit, esophagus, trachea, stomach, intestinal tract, biliary tract, ureter, bladder, vagina, artery and vein. When the biological composite scaffold material is columnar, it generally may be used to prepare materials for repairing ruptures or defects of ligament, achilles tendon or cartilage and the like.

According to specific embodiments of the present invention, soft tissue patches (such as pelvic floor patches, hernia patches, meninges patches, pleura patches, wound surface dressings, abdomen patches, small-caliber arteries and achilles tendons), tubular structure scaffolds (such as arterial scaffolds, external venous support, tracheal scaffolds, esophageal scaffolds, bladder, ureteral and urethral scaffolds, and the like), ligaments, tendons and the like have been successfully prepared from the (super-) hydrophilic electrospinning filaments as mentioned above. Inducing-scaffold materials with respect to bones, cartilages and heart valves are being developed, and corresponding animal or human trials have been conducted. Related experiments indicate that the biological composite scaffold material of the present invention, after implantation in the body, may achieve the following technical effects: (1) within 1-2 weeks after implantation, the infiltration of neutrophils, monocytes and lymphocytes is observed around the implant; at $4^{th}$ week, macrophages and lymphocytes are present around the implant, and collagen fibers may be observed; and at $16^{th}$ week, the material is completely replaced by regenerated tissues with great tissue reaction; (2) within 1 week after implantation, the mechanical strength of the implant decreases continually; and at $2^{nd}$ week the mechanical strength reaches an inflection point and then increases gradually over time; (3) the local occurrence rate of bacterial infection is less than 1% at implantation sites in all animal trials; and in 15 clinical trials of pelvic floor repair, no patch infection cases occur, and no cases have the recurrence of pelvic organ prolapsed after 4 months clinical observation; and (4) the release amount of the loaded antibacterial substances is more than 30% of the load amount within 15 minutes, and thus an antibacterial barrier at a high concentration is formed locally to effectively prevent the formation of bacterial membrane.

SPECIFIC MODE FOR CARRYING OUT THE PRESENT INVENTION

In order to clearly understand the technical features, purposes and effects of the present invention, now the present invention will be further illustrated in details with reference to examples and accompanying figures, but the present invention is not limited in any way. Unless otherwise specified, all the parts are counted by weight in the following examples.

In all examples, each raw material may be purchased commercially. Unless explicitly stated, the used Fg is pig blood-derived; and the mass ratio of polylactic acid to polycaprolactone in P(LLA-CL) is 70:30.

Example 1

The samples in this example were divided into 3 groups:
(1) pure P(LLA-CL) group: 6 g P(LLA-CL) was dissolved in 100 ml hexafluoroisopropanol;
(2) P(LLA-CL)+Fg group: Fg was dissolved in 20 ml saline to obtain solution 1; 6 g P(LLA-CL) was dissolved in 80 ml hexafluoroisopropanol to obtain solution 2; the solutions 1 and 2 were blended, such that there were 4 g Fg and 6 g P(LLA-CL) contained in 100 ml blend solution; and
(3) P(LLA-CL)+Fg+protective agent group: Fg and L-arginine hydrochloride were dissolved in 20 ml saline to obtain solution 1; P(LLA-CL) was dissolved in 80 ml hexafluoroisopropanol to obtain solution 2; the solutions 1 and 2 were blended; such that there were 4 g Fg, 1 g L-arginine hydrochloride and 6 g P(LLA-CL) contained in 100 ml blend solution. The biological composite scaffold material was prepared by electrospinning. The parameters for an electrospinning machine were set as follows: electrospinning distance of 15 cm; electrospinning voltage of 15 kV; solution flow rate of 2 ml/h; and transverse speed of injection syringe of 10 cm/min. The thickness of the electrospinning membrane was about 200 μm.

Figure 1:
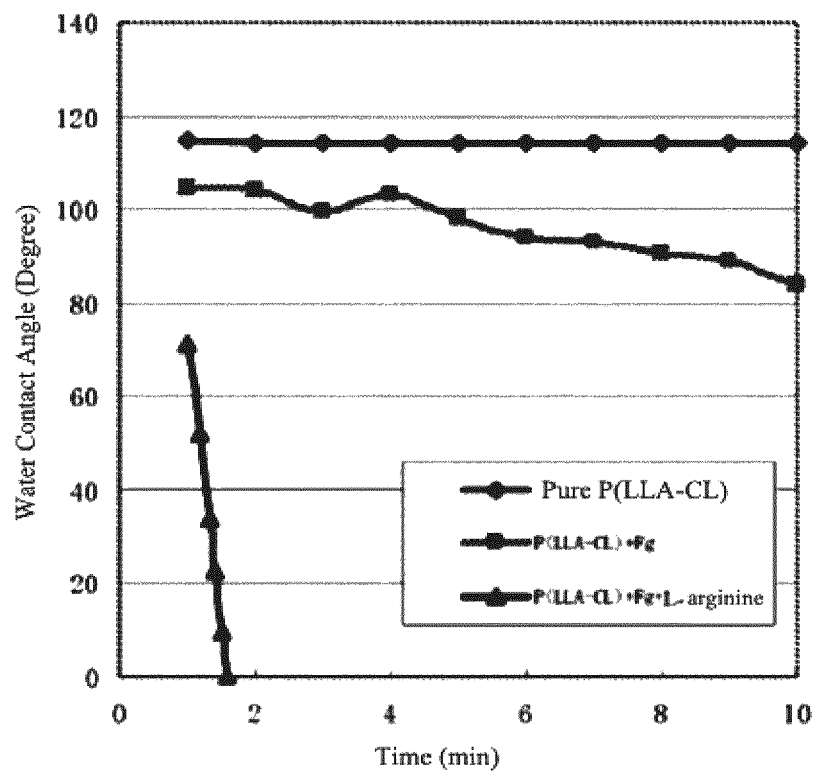
FIG. 1 is a chart showing the test data of surface wettability of electrospinning biological composite scaffold materials according to Example 1 of the present invention.

The initial contact angle and equilibrium contact angle of the samples of the above-mentioned three groups were measured by measuring the change of water contact angle of each electrospinning membrane over time by using a sessile drop method on a OCA20 optical contact angle measuring device, and collecting the contact angle data of the samples in a continuous dynamic tracking measurement mode with a speed of 1 time/s. The measurements were shown in FIG. 1. As shown in FIG. 1, the initial and equilibrium contact angles of the electrospinning membrane of the pure P(LLA-CL) group were 118±1.2°; the initial contact angle of the P(LLA-CL)+Fg group was 102±0.8°, the equilibrium contact angle was 82±1.2°, and the equilibrium time was within 10 minutes; and the initial contact angle of the P(LLA-CL)+Fg+L-arginine hydrochloride group was 73±0.2°, the equilibrium contact angle was less than 5°, and the equilibrium time was within 2 minutes.

In addition, after testing, the samples of the P(LLA-CL)+Fg+protective agent group, after contacting with an aqueous solution, had a total volume shrinkage ratio of 10%-15% and a porosity of more than 40%.

Example 2

Bovine blood-derived Fg with different weights and 1 g L-arginine hydrochloride were dissolved in 20 ml saline to obtain solution 1, and the ratio of Fg/L-arginine hydrochloride of the solution is shown in Table 1; 6 g P(LLA-CL) was dissolved in 80 ml hexafluoroisopropanol to obtain solution 2; the solutions 1 and 2 were blended, and were divided into a total of 13 groups. An electrospinning machine from KATO TECH company (Japan) was used to prepare electrospinning membranes respectively. The parameters for the electrospinning machine were set as follows: electrospinning distance of 15 cm; electrospinning voltage of 15 KV; solution flow rate of 2 ml/h; and transverse speed of injection syringe of 10 cm/min. The thickness of the electrospinning membrane was about 200 μm.

The equilibrium contact angle of the electrospinning membranes of each group was measured by using an OCA20 optical contact angle measuring device (Germany). Results were shown in Table 1.

TABLE 1

Dose-effect relationship between the solute content of 100 ml electrospinning liquid and the equilibrium contact angle of electrospinning membranes

| Solute Content of 100 ml Electrospinning Liquid (g) | | | | | Equilibrium Contact Angle of Electrospinning Membranes (°) |
|---|---|---|---|---|---|
| Fibrinogen | L-arginine Hydrochloride | P(LLA-CL) | L-arginine Hydrochloride/ Fibrinogen | Fibrinogen/ P(LLA-CL) | |
| 14.29 | 1 | 6 | 0.07 | 2.38 | 55 |
| 12.50 | 1 | 6 | 0.08 | 2.08 | 50 |
| 10.64 | 1 | 6 | 0.09 | 1.77 | 45 |
| 9.09 | 1 | 6 | 0.11 | 1.52 | 40 |
| 8.00 | 1 | 6 | 0.13 | 1.33 | 35 |
| 5.00 | 1 | 6 | 0.20 | 0.83 | 5 |
| 4.00 | 1 | 6 | 0.25 | 0.67 | 5 |
| 2.50 | 1 | 6 | 0.40 | 0.42 | 5 |
| 2.00 | 1 | 6 | 0.50 | 0.33 | 5 |
| 1.82 | 1 | 6 | 0.55 | 0.30 | 10 |
| 1.67 | 1 | 6 | 0.60 | 0.28 | 20 |
| 1.20 | 1 | 6 | 0.83 | 0.20 | 35 |
| 0.60 | 1 | 6 | 1.66 | 0.10 | 55 |

It can be seen from Table 1 that, as the ratio of L-arginine Hydrochloride/Fibrinogen gradually increased, the changes in the equilibrium contact angle of electrospinning membranes were divided into three stages: with an increase of the ratio from 0.07 to 0.13, the equilibrium contact angle gradually decreased from 55±1.2° to below 5°; with the ratio from 0.2 to 0.5, the equilibrium contact angle maintained below 5°; and with the ratio from 0.55 to 1.66, the equilibrium contact angle gradually increased again and finally reached more than 55±0.70, making the membrane hydrophobic.

Example 3

4 g Fg and 1 g L-arginine hydrochloride were dissolved in 20 ml saline to obtain solution 1; 6 g P(LLA-CL) was dissolved in 80 ml hexafluoroisopropanol to obtain solution 2; the solutions 1 and 2 were blended such that there were 4 g Fg, 1 g L-arginine hydrochloride and 6 g P(LLA-CL) contained in 100 ml blend solution; and the biological composite scaffold material was prepared by electrospinning. The parameters for an electrospinning machine were set as follows: electrospinning distance of 15 cm; electrospinning voltage of 15 KV; solution flow rate of 2 ml/h; and transverse speed of injection syringe of 10 cm/min. The thickness of the electrospinning membrane was 200-400 μm.

As a biological composite scaffold material, the prepared electrospinning membranes had a thickness of 200-400 μm, a water contact angle of less than 5° and a mechanical strength of 15-20 MPa. After sterilization using 25 KGy electron beam, the obtained material was used as swine abdominal defect patches.

Figure 2:
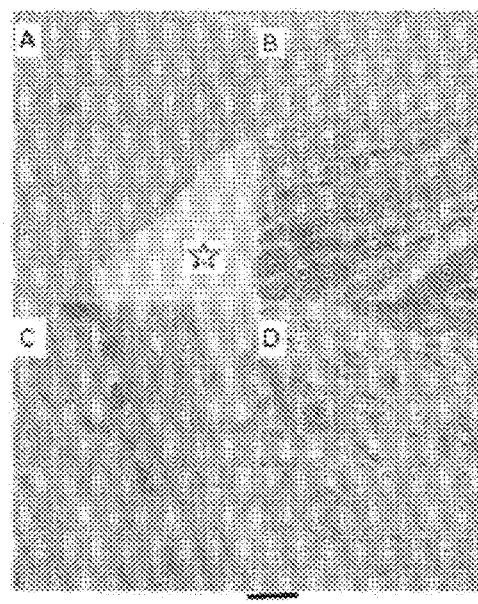
FIG. 2 is the observations at $2^{nd}$ week (Figure A), $2^{nd}$ month (Figure B), $4^{th}$ month (Figure C) and $6^{th}$ (Figure D) after repair using the electrospinning biological composite scaffold material according to Example 3 of the present invention. The position of the implant is indicated by the asterisk in FIG. 2. HE staining. Scale: 100 μm.

30 minipigs (weight: 20-30 kilogram per one) were used in the example. Using midline of abdomen as a dividing line, an abdominal defect (6 cm×8 cm) was made respectively on both sides of the abdomen, all muscles and aponeuroses below dermis were excised and the peritoneum was retained. The defect on one side was repaired with the above-mentioned electrospinning biological composite scaffold material. At $1^{st}$ week, $2^{nd}$ week, $1^{st}$ month, $2^{nd}$ month, $4^{th}$ month and $6^{th}$ month after operation, the general and histological observation of the defect repair sites was conducted respectively after the animals were anesthetized, with each time point 5 animals. It was observed that at $1^{st}$ week after operation, there were local acute inflammatory responses and neutrophils, monocytes and lymphocyte infiltration could be observed around the implant; at $2^{nd}$ week, there still existed the acute inflammatory responses, the degradation of the implant was obvious, and the mechanical strength decreased to a minimum; within 1-4 months, tissue proliferation mainly occurred, the tissue mechanical strength at the implantation site of the implant gradually increased, and the implant completely disappeared at $4^{th}$ month; at $6^{th}$ month, local tissues were replaced by regenerated muscle tissues and fascia tissues, and the mechanical strength reverted to more than 90% of normal tissues. Related results were shown in FIG. 2.

Example 4

2 g Fg and 0.4 g L-arginine hydrochloride were dissolved in 20 ml saline to obtain solution 1; 6 g P(LLA-CL) was dissolved in 80 ml hexafluoroisopropanol to obtain solution 2; the solutions 1 and 2 were blended, such that there were 2 g Fg, 0.4 g L-arginine hydrochloride and 6 g P(LLA-CL) contained in 100 ml blended solution. The blend solution was loaded into an injection syringe which was connected with a blunt 18 G needle at its end, and a stainless steel metal rod was used as a collection device. The injection syringe was placed and fixed on a fixed mount, and then the electrospinning was performed. The parameters for electrospinning were set as follows: electrospinning distance of 15 cm; electrospinning voltage of 15 KV; solution flow rate of 2 ml/h; rotation rate of collection device of 500 rpm; and transverse speed of injection syringe of 10 cm/min. After electrospinning ended, the electrospinning tubular scaffold was intactly taken from the metal rod, and placed in a dry machine for use after its two ends were trimmed. After sterilization using 25 KGy electron beam, the obtained material was used to replace canine external carotid artery.

Figure 3:
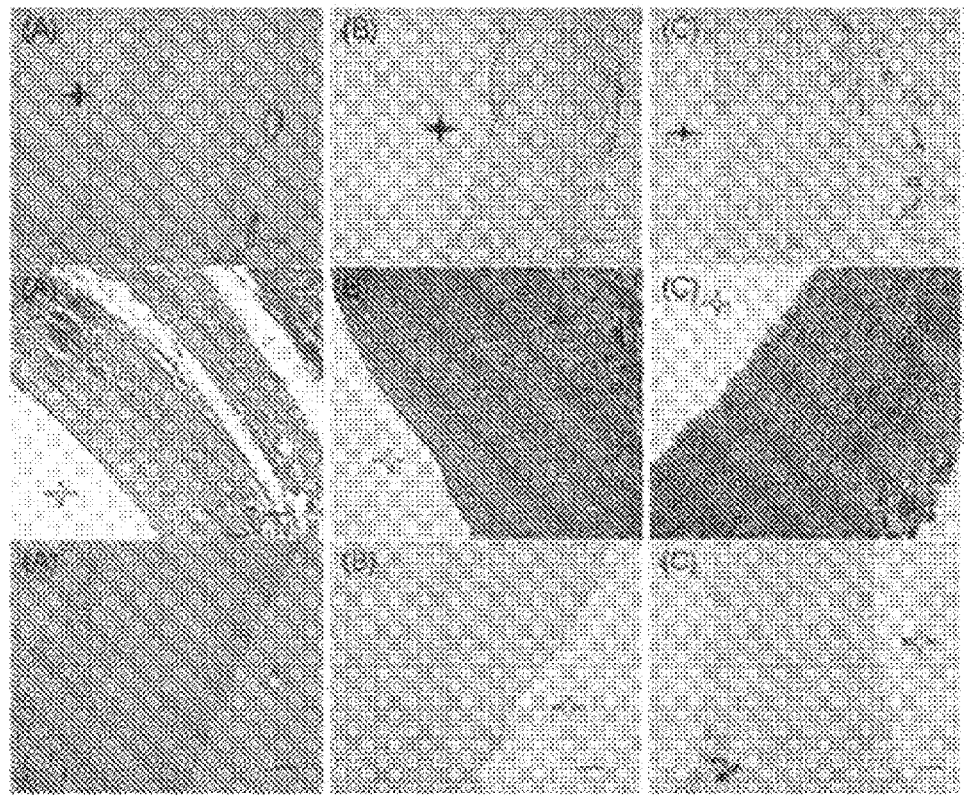
FIG. 3 is the observations of corresponding tissue sections of canine common carotid artery before and after remodeling according to Example 4 of the present invention. Wherein, Figure A: at $2^{nd}$ week after operation; Figure B: at $12^{nd}$ week after operation; and Figure C: normal artery. Upper figure: actin; middle figure: collagen; and lower figure: glycoprotein. The cavity surface of vessels is indicated by the asterisks in FIG. 3.

30 crossbreed dogs (weight: 30-35 kilogram per one) were used in the example. Respectively, the forelimb superficial vein of 3-5 cm in length was taken to obtain vein endothelial cells for performing in vitro proliferation. The dog's own endothelial cells were inoculated at high density on the inner surface of the above-mentioned tubular artery biological composite scaffold material to obtain the experimental group. The group in which the endothelial cells were not inoculated on identical tubular artery biological composite scaffold materials was used as the control group. The tubular scaffold materials of the experimental group and control group were respectively used to replace common carotid artery on both sides. At $1^{st}$ week, $3^{rd}$ week, $1^{st}$ month, $2^{nd}$ month, $4^{th}$ month and $6^{th}$ month after operation, the general and histological observations of artery samples at replacement site were obtained respectively after animals were anesthetized, with each time point 5 animals. Results showed that: the 30 artery substitutes of the control group had a patency rate of 4/5 at $1^{st}$ week and 2/5 at $3^{rd}$ week, and they were all obstructed after $1^{st}$ month; and the 30 substitutes of the experimental group had a patency rate of 4/5 at $1^{st}$ week and 4/5 at $3^{rd}$ week, 5/5 at $1^{st}$ month, 5/5 at $2^{nd}$ month, 5/5 at $4^{th}$ month and 5/5 at $6^{th}$ month, wherein, the inner membranes of unblocked vessel implants of the experimental group all maintained intact; smooth muscle cells appeared within 2 weeks; and middle membrane and outer membrane structure similar to those of a normal artery wall were formed within 4 months. Related results were shown in FIG. 3.

Example 5

2.5 g Fg and 1 g L-arginine hydrochloride were dissolved in 20 ml D-Hank's solution to obtain solution 1; 6 g P(LLA-CL) was dissolved in 80 ml hexafluoroisopropanol to obtain solution 2; the solutions 1 and 2 were blended, such that there were 2.5 g Fg, 1 g L-arginine hydrochloride and 6 g P(LLA-CL) contained in 100 ml blend solution. The electrospinning of the obtained solution was performed. The parameters for an electrospinning machine were set as follows: electrospinning distance of 15 cm; electrospinning voltage of 70 KV; and humidity of less than 20%. The electrospinning membranes had a thickness of 250-300 μm, a contact angle of less than 5 and a tensile strength of 10-20 MPa.

After sterilization using 25 KGy electron beam, the obtained material was used as pelvic floor patches.

30 clinical pelvic organ prolapse patients aged 45-80 were chosen, with anterior vaginal walls at II-VI level classified according to POP-Q grading and MRI grading. The patients were randomly divided into an experimental group and a control group, with each group having 15 patients. The experimental group used the biological composite scaffold material as the repair material, and the control group used polypropylene as the repair material. The implants were implanted into the anterior vaginal wall via vaginal approach, respectively. The patients were followed up at $1^{st}$ week, $1^{st}$ month, $3^{rd}$ month and $6^{th}$ month after operation. The follow-up results indicated that, at $1^{st}$ month, $3^{rd}$ month and $6^{th}$ month after operation, 30 patients of the experimental and control groups were at 0-I level according to the POP-Q grading. After quantitative measurement of the hardness of the anterior vaginal wall using Intervention Ultrasound Indentation System, at $3^{rd}$ month and $6^{th}$ month after operation, for the experimental group, the hardness parameter values of the anterior vaginal wall were 120±8.2 KPa and 60±5.8 (KPa); and for the control group, the hardness parameter values were 250±16 KPa and 360±30.4 KPa.

Example 6

2.5 g Fg and 0.5 g L-arginine were dissolved in 20 ml water for injection to obtain solution 1; 6 g P(LLA-CL) was dissolved in 80 ml hexafluoroisopropanol to obtain solution 2; the solution 1 and 2 were blended, such that there were 2.5 g Fg, 0.5 g L-arginine hydrochloride and 6 g P(LLA-CL) contained in 100 ml blend solution. The electrospinning of the obtained solution was performed. The parameters for the electrospinning machine were set as follows: electrospinning distance of 15 cm; electrospinning voltage of 70 KV; humidity of less than 20%; solution flow rate of 2 ml/h; and transverse speed of injection syringe of 10 cm/min. The electrospinning membranes had a thickness of 250-300 μm, a contact angle of less than 5° and a tensile strength of 10-20 MPa. The obtained membranous material was cut into a rectangular or square shape and rolled up for 3-4 laps to form a cylinder with a diameter of 3-5 mm and a length of 3-10 mm. After sterilization using 25 KGy electron beam, the obtained material was used as a substitute for canine achilles tendon and anterior cruciate ligament.

6 beagles (weight: 20-30 kilogram per one) were chosen. After general anesthesia, the hindlimb achilles tendon on one side was cut off, and the cylinder scaffold material with a diameter of 3 mm was anastomosed end-to-end with both ends of the achilles tendon. It was observed that, within 2 weeks after operation, the operated canine limb could not touch the ground and the dog walked using a single hindlimb; at $3^{rd}$-$4^{th}$ week after operation, the operated limb begun to strike the ground and the dog limped; at $2^{nd}$ month after operation, 6 experimental dogs all walked with no difficulties; and at $6^{th}$ month after operation, there is no difference between the diameter of the achilles tendon on the operation side and that on the opposite side.

Figure 4:
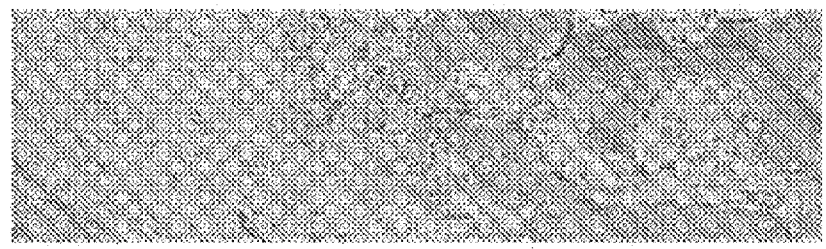
FIG. 4 is the results of histological examination for the implantation site of the ligament implant at $52^{nd}$ week after operation according to Example 6 of the present invention, which shows no obvious differences from normal ligament tissues.

6 adult beagles (weight: 15-20 kilogram per one) received unilateral hindlimb anterior cruciate ligament (ACL) replacement. They were put on general anesthesia and in bent-knee position. The ligament was cut off at the bilateral attachments of ACL on the operation side. A bone tunnel with a diameter of 4.5 mm was drilled on the thighbone and the shinbone at the attachments of both ACL ends. The above-mentioned cylinder biological composite scaffold material with a diameter of 4 mm was implanted into joint under pressures imposed by hand. The intra-articular length of the biological composite scaffold material was about 10 mm. All screws were located at the front side of the kneecap of the bone fragment and the cortical bone surface of the bone fragment was held to the wall of the bone tunnel. Activities are not restricted after operation. At $8^{th}$ week after operation, all animals did not have obviously abnormal gait; and at $52^{nd}$ after operation, the animals were sacrificed to conduct the general and histological observation. It was found that the ratio of strength, stiffness and stress of the reconstruction to those of ACL on the control side had a trend of increasing gradually, and was 46%, 70% and 85% of the control side, respectively. Histological examination showed no significant differences between the histological appearance of the experimental side and the control side. Related results were shown in FIG. 4.

Example 7

1.2 g Fg and 1 g L-arginine were dissolved in 20 ml D-Hank's solution to obtain solution 1; 6 g P(LLA-CL) (the mass ratio of polylactic acid to polycaprolactone was 95:5) was dissolved in 80 ml trichloromethane to obtain solution 2; the solution 1 and 2 were blended, such that there were 1.2 g Fg, 1 g L-arginine and 6 g P(LLA-CL) contained in 100 ml blend solution. The electrospinning of the obtained solution was performed. The blend solution was loaded into an injection syringe which was connected with a blunt 18 G needle at its end, and a stainless steel metal rod was used as a collection device. The injection syringe was placed and fixed on a fixed mount, and then the electrospinning was performed. The parameters for the electrospinning machine were set as follows: electrospinning distance of 15 cm; electrospinning voltage of 15 kV; solution flow rate of 2 ml/h; rotation rate of the collection device of 500 rpm; and transverse speed of the injection syringe of 10 cm/min. After electrospinning ended, the electrospinning tubular scaffold was intactly taken from the metal rod, and placed in a dry machine for use after its two ends were trimmed. The tubular biological composite scaffold material with a wall thickness of 200-300 m, a inner diameter of 20 mm and a length of 6-8 cm, possessed a water contact angle of 30-40° and a mechanical strength of 10-15 MPa. After sterilization using 25 KGy electron beam, the obtained material was used to replace the esophagus of beagles.

Figure 5:
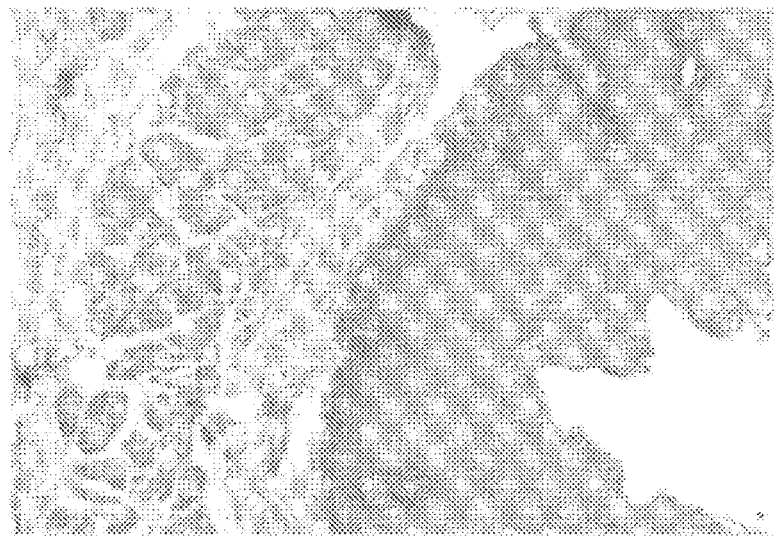
FIG. 5 is the observations of the regenerated esophagus under a microscope at $6^{th}$ month after operation in Example 7 of the present invention. It showed that the wall thickness of the regenerated esophagus was the same as that of the esophagus in situ. Under a microscope, the cavity surface of the regenerated esophagus specimen had intact stratified squamous epithelium, below which there were a submucosa composed of loose connective tissues and a muscular layer composed of a mix of skeletal muscles and smooth muscles. The outer membrane was loose connective tissue comprising larger vessels, lymphatic vessels and nerves.

For 6 adult beagles (weight: 15-20 kilogram per one), after general anesthesia, the chest was entered through the fourth intercostal space via a right posterolateral incision. Thorax esophagus having a length of about 8 cm was isolated and excised, and then the tubular scaffold material of 6 cm length was implanted in situ and anastomosed end-to-end to reconstruct the esophagus. The scaffold material was wrapped with pleura and the chest was closed layer by layer. Drainage and anti-infection were performed after operation. At $2^{nd}$ week after operation, the normal diet was fed. At $6^{th}$ month after operation, the animals were sacrificed without anesthesia and the general and pathological observation was conducted: under a gastroscope, it could be observed that the esophageal mucosa was intact and smooth and had the same color as the esophageal mucosa in situ and the lumen was unobstructed; and for general samples, a uniform white and soft muscular conduit could be observed. The wall thickness of the regenerated esophagus was the same as that of the esophagus in situ. Under a microscope, the cavity surface of the regenerated esophagus specimen had intact stratified squamous epithelium, below which there were a submucosa composed of loose connective tissues and a muscular layer composed of skeletal muscles and smooth muscles. The outer membrane was loose connective tissues comprising larger vessels, lymphatic vessels and nerves. Related results were shown in FIG. 5.

Example 8

8 g Fg and 1 g L-arginine hydrochloride were dissolved in 20 ml D-Hank's solution to obtain solution 1; 6 g P(LLA-CL) (the mass ratio of polylactic acid to polycaprolactone was 20:80) was dissolved in 80 ml hexafluoroisopropanol to obtain solution 2; the solution 1 and 2 were blended, such that there were 8 g Fg, 1 g L-arginine hydrochloride and 6 g P(LLA-CL) contained in 100 ml blend solution. The electrospinning of the obtained solution was conducted. The parameters for the electrospinning machine were set as follows: electrospinning distance of 15 cm; electrospinning voltage of 70 kV; and humidity of less than 20%. The prepared membranous biological composite scaffold material having a wall thickness of 200-300 m, possessed a water contact angle of 30-40° and a mechanical strength of 10-15 MPa. After sterilization using 25 KGy electron beam, it was used to repair the bladder defect of New Zealand White rabbits.

Figure 6:
FIG. 6 is the observations of the bladder tissue at $6^{th}$ month after operation according to Example 8 of the present invention. It showed that the regenerated bladder had the same structure and capacity as a normal bladder and possessed normal contraction function; and the repair area had intact bladder mucous layer, muscle layer and outer membrane.

For 3 New Zealand White rabbits (weight: 1.5-2.5 kilogram per one), after general anesthesia, 40% of the anterior wall of the bladder was excised via transperitoneal approach and the above-mentioned electrospinning scaffold material was used to repair the bladder. At 6th month after operation, the regenerated bladder had the same structure and capacity as a normal bladder and possessed a normal contraction function; and the repair area had an intact mucous layer, muscle layer and outer membrane. Related results were shown in FIG. 6.

Example 9

1.6 g Fg and 0.5 g L-arginine hydrochloride were dissolved in 20 ml D-Hank's solution to obtain solution 1; 6 g P(LLA-CL) was dissolved in 80 ml hexafluoroisopropanol to obtain solution 2; the solution 1 and 2 were blended, such that there were 1.6 g Fg, 0.5 g L-arginine hydrochloride and 6 g P(LLA-CL) contained in 100 ml blend solution. The electrospinning of the obtained solution was conducted to prepare a membranous biological composite scaffold material having a wall thickness of 300-400 m, a equilibrium contact angle of 20° and a mechanical strength of 10-20 MPa. After sterilization using 25 KGy electron beam, it was used to repair the meninges defect of New Zealand White rabbits.

Figure 7:
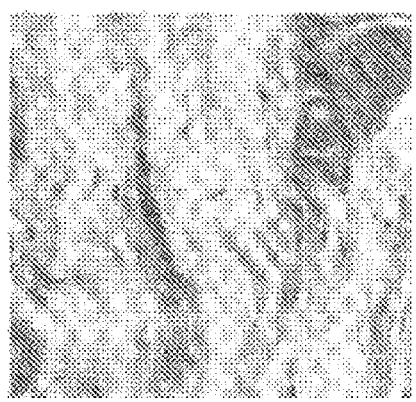
FIG. 7 is the histological observations of the meninges tissue at $6^{th}$ month after operation according to Example 9 of the present invention. Under a microscope, irregular dense connective tissues could be observed, in which bulky collagen fibers in different directions interweaved with each other and formed a dense lamellae structure, with small amount of matrix and fibroblasts between the fibers.

5 New Zealand White rabbits (weight: 2-3 kilogram per one) were taken. After general anesthesia, the skull was exposed under a sterile condition, on both sides of the posteromedial line of coronal suture, one bone window with a diameter of 1.2 cm was made using a high speed drill, respectively. The dura was exposed. The right side was the experimental group, in which autologous dura (0.8×0.8 cm) was excised and the above-mentioned biological composite scaffold material was sutured with silk thread. As a normal control, the dura on the left side was untreated. Conventional anti-infection was performed. At 6th month after operation, the animals were sacrificed after anesthesia, and the general and histological observation of the operation site was conducted. All animals did not have local swelling and cerebrospinal fluid fistula, and the incision healing was good. The general observation showed that the internal layer of the operation site on the right side was smooth, the outer layer thereof was rough; its fiber orientation was mainly presented as arcuate fibers, radiate fibers, longitudinal fibers and diagonal fibers; and vascular network distribution was visible. Under a microscope, irregular dense connective tissues could be observed, in which bulky collagen fibers in different directions interweaved with each other and formed a dense lamellae structure, with small amount of matrix and fibroblasts between the fibers. Related results were shown in FIG. 7.

Example 10

2.5 g Fg, 1 g L-arginine hydrochloride, and 534,000 U gentamicin were dissolved in 20 ml saline to obtain solution 1; 6 g P(LLA-CL) was dissolved in 80 ml hexafluoroisopropanol to obtain solution 2; the solution 1 and 2 were blended. An electrospinning machine from KATO TECH company (Japan) was used to prepare electrospinning membranes. The parameters for the electrospinning machine were set as follows: electrospinning distance of 15 cm; electrospinning voltage of 15 KV; solution flow rate of 2 ml/h; and transverse speed of injection syringe of 10 cm/min. The gentamicin content of the obtained electrospinning membrane was 60,000 U/g or 101.6 U/cm$^2$. The in vitro release of gentamicin was measured according to dilution method in the appendix of *Pharmacopoeia of People's Republic of China* (2000). 3 pieces of membranes were taken before and after irradiation, respectively, and precisely cut into membranes of 6 g, and placed in water bath at 32° C. with PBS (PH 7.2) as a release medium. 5 ml solution was sampled from each group at 0.25, 0.5, 1, 12, 24, 48 and 96 hour, respectively. Derivatization reaction operations were performed. Absorbance was measured at a wavelength of 356 nm. According to the standard curve equation, the release amount of each piece of the electrospinning samples at different time points was calculated so as to calculate accumulated release percentage at each time point. Results are shown in Table 2.

TABLE 2

Testing Results of the In Vitro Release of Gentamicin

| Drug Release | Accumulated Release Percentage of Gentamicin (%) | |
| --- | --- | --- |
| Time (h) | Before Irradiation | After Irradiation |
| 0.25 | 62.12 ± 1.34 | 61.12 ± 2.31 |
| 0.5 | 64.24 ± 0.98 | 63.80 ± 1.50 |
| 1 | 82.86 ± 3.12 | 64.20 ± 1.32 |
| 12 | 84.12 ± 1.23 | 65.30 ± 2.50 |
| 24 | 84.52 ± 2.43 | 68.50 ± 2.60 |
| 48 | 87.40 ± 2.50 | 70.21 ± 3.40 |
| 96 | 88.90 ± 2.10 | 72.42 ± 2.54 |

It can be seen from Table 2 that, gentamicin was rapidly released to a peak within 15 minutes, then slowly released and lasted to the 5th day (120 h), before or after irradiation.

What is claimed is:

1. A hydrophilic electrospinning biological composite scaffold material, wherein it is prepared by blending an aqueous solution of fibrinogen and L-arginine or hydrochloride thereof with a P(LLA-CL) solution using an electrospinning technique, wherein the hydrophilic electrospinning biological composite scaffold material has an equilibrium contact angle, and the equilibrium contact angle thereof is less than 55°.

2. The hydrophilic electrospinning biological composite scaffold material according to claim 1, wherein the fibrinogen is derived from fibrinogen of mammals.

3. The hydrophilic electrospinning biological composite scaffold material according to claim 1, wherein in the aqueous solution of fibrinogen and L-arginine or hydrochloride thereof, the mass ratio of fibrinogen to L-arginine or hydrochloride thereof is 1.2:1-12.5:1.

4. The hydrophilic electrospinning biological composite scaffold material according to claim 1, wherein the mass ratio of polylactic acid to polycaprolactone in the P(LLA-CL) is 20:80-95:5.

5. The hydrophilic electrospinning biological composite scaffold material according to claim 1, wherein the aqueous solution of fibrinogen and L-arginine or hydrochloride thereof comprises solvents selected from the group consisting of pure water, water for injection, salt solutions, buffers and cell culture media.

6. The hydrophilic electrospinning biological composite scaffold material according to claim 5, wherein the salt solutions are selected from sodium chloride solution and potassium chloride solution; the buffers are selected from phosphate buffer, Tris-HCl buffer, glycine buffer and D-Hank's solution; and the cell culture media are selected from DMEM medium, 1640 medium and MEM medium.

7. The hydrophilic electrospinning biological composite scaffold material according to claim 1, wherein the aqueous solution of fibrinogen and L-arginine or hydrochloride thereof comprises one or more solvents selected from the group consisting of hexafluoroisopropanol, trichloromethane, dimethylformamide, tetrahydrofuran, chloroform and acetone.

8. The hydrophilic electrospinning biological composite scaffold material according to claim 1, wherein after the aqueous solution of fibrinogen and L-arginine or hydrochloride thereof is blended with the P(LLA-CL) solution, the mass ratio of fibrinogen to P(LLA-CL) is 0.2:1-2.1:1.

9. The hydrophilic electrospinning biological composite scaffold material according to claim 1, wherein after contacting with an aqueous solution, the total volume shrinkage ratio is not more than 20% and the porosity is not less than 30%.

10. The hydrophilic electrospinning biological composite scaffold material according to claim 1, wherein the aqueous solution of Fibrinogen and L-arginine or hydrochloride thereof is further loaded with antibacterial substances which are one or more substances selected from penicillins, cephalosporins, carbapenms, aminoglycosides, tetracyclines, macrolides, glycosides, sulfonamides, quinolones, nitroimidazoles, lincosamides, phosphonomycin, chloromycetin, polymyxin B and bacitracin.

11. The hydrophilic electrospinning biological composite scaffold material according to claim 10, wherein the penicillins are selected from penicillin, ampicillin and carbenicillin; the cephalosporins are selected from cephalexin, cefuroxime sodium, ceftriaxone and cefpirome; the carbapenms are thiomycin; the aminoglycosides are selected from gentamicin, streptomycin and kanamycin; the tetracyclines are selected from tetracycline and chlortetracycline; the macrolides are selected from erythromycin and azithromycin; the glycosides are vancomycin; the sulfonamides are selected from sulfadiazine and trimethoprim; the quinolones are selected from pipemidic acid and ciprofloxacin; the nitroimidazoles are selected from metronidazole and tinidazole; and the lincosamides are selected from lincomycin and clindamycin.

12. The hydrophilic electrospinning biological composite scaffold material according to claim 10, wherein the antibacterial substances is released not less than 30% of total load amount within 15 minutes after the implantation of the scaffold material.

13. The hydrophilic electrospinning biological composite scaffold material according to claim 1, wherein the biological composite scaffold material is membranous and has a thickness of 10-1500 μm.

14. The hydrophilic electrospinning biological composite scaffold material according to claim 1, wherein the biological composite scaffold material is tubular, and the tube wall thereof has a thickness of 1-1500 m and the internal diameter thereof is 2-200 mm.

15. The hydrophilic electrospinning biological composite scaffold material according to claim 1, wherein the biological composite scaffold material is columnar, and the diameter thereof is 2-20 mm.

16. A method of preparing the hydrophilic electrospinning biological composite scaffold material according to claim 1, comprising:

blending an aqueous solution of fibrinogen and L-arginine or hydrochloride with a P(LLA-CL) solution and subjecting the obtained solution to electrospinning by using an electrospinning technique, to prepare the biological composite scaffold material.

17. The method according to claim 16, wherein in the electrospinning technique, the parameters for an electrospinning machine are set as follows: electrospinning distance of 10-30 cm; electrospinning voltage of 15-70 kV; and solution flow rate of 2-400 ml/h.

18. The method according to claim 16, wherein the method further comprises performing the sterilization of the prepared biological composite scaffold material by using 15-35 KGy ionizing radiation.

19. Application of the hydrophilic electrospinning biological composite scaffold material according to claim 1, for using as the material for the repair of body tissue defects or using for the preparation of the material for repairing body tissue defects, the application comprising implanting the repair material in the body of a subject in need thereof.

20. The application according to claim 19, wherein the biological composite scaffold material is membranous and used in the preparation of repair materials for the treatment of meninges defects, abdominal defects, pelvic organ prolapse, atrium defects, ventricular septum defects, pericardium defects, tendon or ligament rupture, or parenchymatous organ rupture.

21. The application according to claim 19, wherein the biological composite scaffold material is tubular and used to prepare repair materials for repairing tubular organ defects, and the tubular organ comprises one or more selected from nerve conduit, esophagus, trachea, stomach, intestinal tract, biliary tract, ureter, bladder, vagina, artery and vein.

22. The application according to claim 19, wherein the biological composite scaffold material is columnar and used to prepare repair materials for repairing the rupture or defect of ligament, achilles tendon or cartilage.

23. The hydrophilic electrospinning biological composite scaffold material according to claim 2, wherein the mammals are humans, pigs, cattle, sheep or horses.

24. The hydrophilic electrospinning biological composite scaffold material according to claim 13, wherein the biological composite scaffold material has a thickness of 50-500 μm.

25. The hydrophilic electrospinning biological composite scaffold material according to claim 14, wherein the tube wall has a thickness of 50-500 μm.

* * * * *